United States Patent
Belcheff

(10) Patent No.: US 6,592,909 B2
(45) Date of Patent: Jul. 15, 2003

(54) FOOD SUPPLEMENT

(76) Inventor: Elsie Belcheff, Box 179 Margo, Saskatchewan (CA), S0A 2M0

(*) Notice: Subject to any disclaimer, the term of this patent is extended or adjusted under 35 U.S.C. 154(b) by 0 days.

(21) Appl. No.: 09/735,470

(22) Filed: Dec. 14, 2000

(65) Prior Publication Data

US 2001/0031283 A1 Oct. 18, 2001

Related U.S. Application Data

(60) Provisional application No. 60/139,489, filed on Jun. 17, 1999.

(51) Int. Cl.$^7$ .......................... A01N 65/00; A61K 35/78
(52) U.S. Cl. ........................................ 424/725
(58) Field of Search .......................................... 424/725

(56) References Cited

U.S. PATENT DOCUMENTS 5,869,060 A * 2/1999 Yoon et al. ................. 424/725

OTHER PUBLICATIONS

Web Site: http://em outreach.sdsc.edu/web course/ReadList EM.html–Part II.A.6.(a) Freeze–Drying–pp. 1–5 & Reading Lis F: [Freeze drying] Nermut, M.V. "Freeze–drying for electron microscopy" Princ. Tech. Elec. Microsc 7:79–117.*

* cited by examiner

*Primary Examiner*—Herbert J. Lilling
(74) *Attorney, Agent, or Firm*—Michael R. Williams; Adrian D. Battison; Ryan W. Dupuis

(57) ABSTRACT

A method of preparing an extract from purslane such that the medicinal and nutritional properties of the plant do not degrade is herein described. The extract is suitable for use as a nutritional supplement or as part of a medicinal or pharmaceutical composition for treating a variety of ailments. The supplement has a complete and balanced formula for supplying everything the body needs and has the energy to help the body repair itself.

2 Claims, No Drawings

FOOD SUPPLEMENT

This application claims benefit to Provisional Application Ser. No. 60/139489 filed Jun. 17, 1999.

FIELD OF THE INVENTION

The present invention relates generally to the field of supplements. More specifically, the present invention relates to a supplement having purslane as the active ingredient.

BACKGROUND OF THE INVENTION

Purslane (*Portulaca oleraceais*) is a smooth, low growing succulent plant with reddish stems. It has small yellow flowers which produce many sand-sized black seeds. Furthermore, Purslane is an annual that reproduces by seeds.

Purslane contains Ω-3 fatty acids, which some research indicates is useful in preventing heart attacks, Ω-6 fatty acids, silicone, calcium and amino acids as well as other nutritionally-important components. Thus, purslane has considerable nutritional benefits but has not been widely exploited.

In addition, the plant has long been held to have medicinal properties as there are reports of using purslane to treat arthritis and inflammation. Specifically, botanical.com notes that "the expressed juice taken while fresh, was said to be good for strangury, and taken with sugar and honey to afford relief for dry coughs, shortness of breath and immoderate thirst, as well as for external application in inflammation and sores". However, one of the problems with purslane is that these properties appear to be short-lived, meaning that the purslane must be used while fresh.

Given the medicinal and nutritional properties of purslane described above, it is evident that supplements prepared from purslane such that these properties were retained or stabilized would be beneficial.

SUMMARY OF THE INVENTION

According to a first aspect of the invention, there is provided a method of preparing a natural extract comprising: providing a quantity of purslane; blending the purslane, thereby forming a mixture; and freezing the mixture.

The frozen mixture may be dehydrated or freeze dried so as to form a powder.

The mixture may include a preservative, for example, a natural preservative. The natural preservative may be apple juice.

The purslane may comprise purslane plants except the roots.

The purslane may be at seeding stage.

According to a second aspect of the invention, there is provided a pharmaceutical composition comprising as the active ingredient purslane and a suitable excipient.

According to a third aspect of the invention, there is provided a medicinal composition comprising as the active ingredient purslane and a preservative.

The medicinal composition may be in the form of a powder, tablet, capsule, cream, lotion or salve.

The invention will now be described by way of examples; however, the invention is not intended to be limited to the examples.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

In the example described herein, purslane plants are processed into a powdered extract. As will be appreciated by one knowledgeable in the art, this powder may be used directly as a supplement or may be combined with other articles to produce medicinal creams, salves and lotions, pharmaceutical compositions such as powders, pills and capsules or nutritional supplements using means known in the art. Clearly, compositions such as these could be used as nutritional supplements, anti-inflammatory treatments, bowel, blood and liver cleansers or for treating or preventing osteoporosis.

As discussed above, purslane contains high levels of several biologically important compounds and minerals, including Ω-3 fatty acids, which some research indicates is useful in preventing heart attacks, Ω-6 fatty acids, antioxidants, silicon, calcium, protein, fiber, zinc, iron and phosphate among others. Furthermore, the plant itself has been used previously to treat arthritis and inflammation, among other ailments. However, these medicinal properties do not appear to be long-lived in the native plant. That is, as discussed above, it has always been stated that the purslane must be used fresh.

When prepared as described below, the supplement made from purslane has been shown to: control yeast infections; shrink enlarged prostates (due to the high level of zinc in the plant); help impotence; increase the body's supply of estrogen and progesterone (high in magnesium, citrate, aspartate, acetate and vitamin Bs); support the adrenals, thereby reducing stress; promote repair of cellular damage throughout the body; smooth and soften skin; and provide energy.

In the example described herein, purslane plants are picked while at seed. It is important to note that the growth stage of the plant appears to be very important so that the maximal benefits be obtained. However, plants at other stages of development may be used in other embodiments.

The plants are washed and the roots are then cut off and discarded. The remaining plant material, including the seeds, is then placed in a blender. It is of note that the seeds are included in this embodiment as they provide fiber.

In some embodiments, a liquid having preservative properties may be added to the plant material in the blender. In this embodiment, apple juice is utilized, although as will be appreciated in the art, other materials that stabilize the active ingredients of purslane may also be used. Alternatively, other natural juices, for example, tomato juice, may be used. The mixture is then blended, producing an extract. Specifically, as the purslane is a succulent plant, the plant material dissolves readily in the apple juice, thereby forming an extract. Furthermore, the chemical properties of the apple juice, specifically, the sugar and water content, act to stabilize the active ingredients in the purslane.

The extract is then frozen, in some embodiments, into ice cubes. At this time, the extract ice cubes may be used directly as supplements by adding them directly to beverages. Alternatively, the frozen extract may be freeze-dried, thereby producing a powder. It is of note that in some embodiments, water is added back to the frozen extract during the freeze-drying process.

In other embodiments, the plant material is blended and frozen without the addition of a preservative.

In some embodiments, the frozen blended plant material, either with or without a preservative, may be dehydrated using means known in the art. For example, the frozen material may be dehydrated at 125° F. for 12 hours to form a powder. Alternatively, other methods of dehydration known in the art may be used.

As discussed above, purslane contains high levels of several biologically important compounds and minerals, for example, Ω-3 fatty acids, Ω-6 fatty acids, anti-oxidants, silicon, calcium, protein, fiber, zinc, iron and phosphate. Furthermore, purslane also contains high levels of protein and enzymes. As such, the powdered extract prepared as described above can be used on its own or combined with other compounds known in the art as a nutritional supplement.

As discussed above, the plant itself has been used previously to treat arthritis and inflammation, among other ailments, although these medicinal properties do not appear to be long-lived. However, as discussed above, the combination of the apple juice and the purslane plants produces an extract that is stable and retains these medicinal properties. As such, the above-described extract may be combined with binders, carriers and excipients known in the art to produce a variety of pharmaceutical and medicinal compositions, such as medicinal creams, salves, lotions, powders, pills and capsules. These could in turn be used as anti-inflammatory treatments, bowel, blood and liver cleansers or for treating or preventing osteoporosis, among others.

Thus, the supplement has a complete and balanced formula for supplying everything the body needs and has the energy to help the body repair itself.

While the preferred embodiments of the invention have been described above, it will be recognized and understood that various modifications may be made therein, and the appended claims are intended to cover all such modifications which may fall within the spirit and scope of the invention.

What is claimed is:

1. A method of preparing a powder extract comprising:

providing a quantity of purslane;

freezing the purslane; and freeze-drying the frozen purslane, thereby forming a powder extract, wherein the powder extract is a natural extract of purslane plant material.

2. The method according to claim 1 wherein the purslane is at seeding stage.

* * * * *